United States Patent [19]
Werder et al.

[11] 4,113,436
[45] Sep. 12, 1978

[54] AUTOMATIC ANALYSIS APPARATUS

[75] Inventors: Roger Daniel Werder, Möhlin; Linus Meier, Effretikon; Karl Lang, Uerikon, all of Switzerland

[73] Assignee: Mettler Instrumente AG, Greifensee, Switzerland

[21] Appl. No.: 551,517

[22] Filed: Feb. 10, 1975

[30] Foreign Application Priority Data

Feb. 15, 1974 [CH] Switzerland .................. 2119/74

[51] Int. Cl.² ..................... G01N 1/14; G01N 33/16
[52] U.S. Cl. ..................... 422/65; 23/230 R; 422/67; 422/68
[58] Field of Search ............ 23/259, 253 R, 230 R; 141/1, 101, 130, 170, 283

[56] References Cited
U.S. PATENT DOCUMENTS

| 3,545,933 | 12/1970 | Podschadly | 23/253 R |
| 3,635,394 | 1/1972 | Natelson | 23/259 |
| 3,751,985 | 8/1973 | Knedel | 23/230 R X |
| 3,796,544 | 3/1974 | Zauft et al. | 23/253 R |
| 3,832,135 | 8/1974 | Drozdowski | 23/230 R |
| 3,854,507 | 12/1974 | Nishioka | 23/259 X |
| 3,897,216 | 7/1975 | Jones | 23/253 R |
| 4,058,367 | 11/1977 | Gilford | 23/253 R |

*Primary Examiner*—Morris O. Wolk
*Assistant Examiner*—Michael S. Marcus
*Attorney, Agent, or Firm*—Hans Berman

[57] ABSTRACT

Operating stations of an automatic analysis apparatus are arranged along a path in which a specimen to be analyzed is moved in a container on a carrier. The specimen is transferred from the carrier to a container supporting platform of each station where it is to be processed, thereby permitting another specimen to by-pass the same station. Different sequences of operations may be performed simultaneously on several specimens without interfering with each other.

14 Claims, 3 Drawing Figures

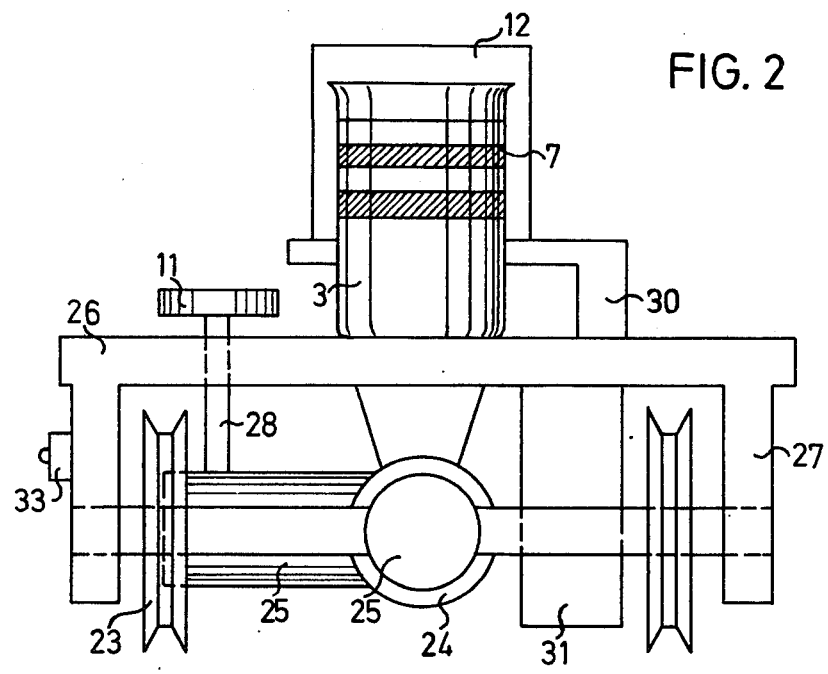

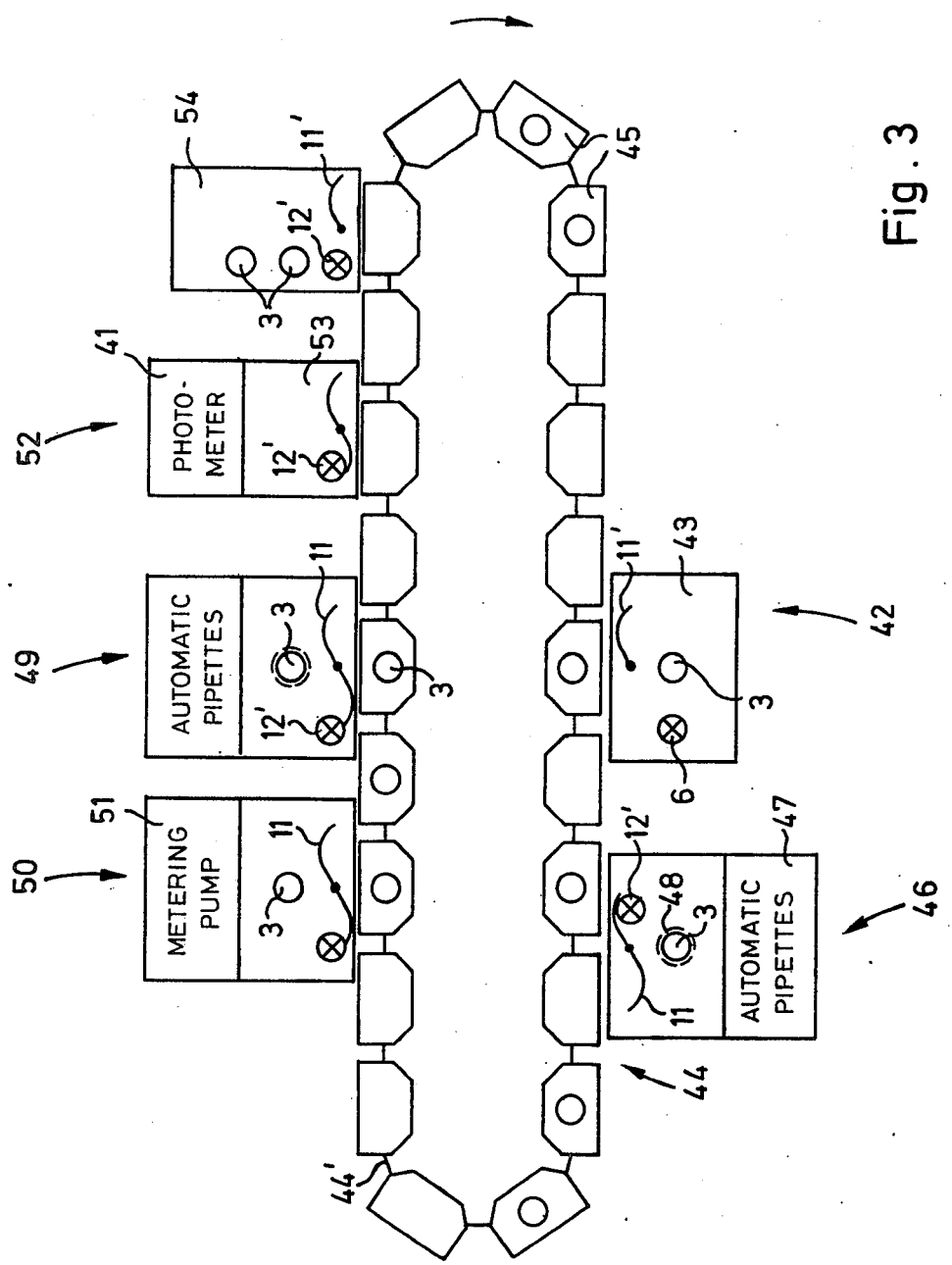

AUTOMATIC ANALYSIS APPARATUS

This invention relates to automatic analysis of specimens for chemical or physical properties, and particularly to apparatus for performing a multiple-step analysis and to a method of operating the apparatus.

In known apparatus for performing a multiple-step analysis, a specimen sequentially enters as many operating stations as there are steps in the procedure. The stations are automatically controlled, and the apparatus ultimately furnishes a signal indicative of the analysis result. It is a disadvantage of this in-line arrangement that the dwell time of a specimen in each station is equal to the dwell time required in the most time consuming step, whereby the capacity of the apparatus is limited.

If the known apparatus is modified to make it suitable for performing different sequences of operation, individual specimens do not utilize all stations, yet their progress through the apparatus is hampered by other specimens processed at the non-utilized stations. The number of different analyses which may be performed advantageously on such in-line apparatus is limited by the length of the processing time. A substantial number of the available operating stations is not in use at any given moment.

Some analytical procedures require the same operation, such as stirring or heating, to be performed repeatedly on the same specimen. In an in-line type of automatic analysis apparatus, several identical stations need to be provided to perform the repeated identical steps.

It is a primary object of this invention to avoid the shortcomings on the afore-described in-line apparatus. More specifically, the invention aims at increasing the capacity of analysis apparatus, at better utilization of individual operating stations, and at greater versatility of the apparatus than is possible with an in-line arrangement of operating stations.

With these and other objects in view, the invention provides analysis apparatus in which a track defines an elongated path and a carrier is adapted to move on the track in the path while carrying a specimen container. Stations spaced along the track include each a container support adjacent the track on which the carrier is moved by a suitable drive. A transfer device permits a container to be transferred between the carrier and the container support of each station when the carrier is aligned with the station transversely of its path. At least one of the stations includes a dosing arrangement for introducing a predetermined amount of liquid into a container supported on the container support of the one station. A central control arrangement operates the carrier drive, the transfer device, and the dosing arrangement.

When such apparatus is operated according to the invention, a specimen is received in each of a plurality of containers, and each specimen receiving container is moved in a predetermined path along a row of operating stations. The specimen received in a first container is mixed with a liquid at a first station, and a property of the mixture so produced is determined at a second station. Prior to the mixing, the first container is shifted from the path to the first station which is transversely offset from the path a distance sufficient to permit a second container to move past the first station during mixing of the specimen received in the first container. After the mixing, the first container is returned to the path.

Other features, additional objects, and many of the attendant advantages of this invention will readily be appreciated as the same becomes better understood by reference to the following detailed description of preferred embodiments when considered in connection with the appended drawing in which:

FIG. 2 shows the movable container carrier in the apparatus of FIG. 1 in front elevation on a larger scale; and FIG. 3 illustrates a second embodiment of the invention in the manner of FIG. 1, some devices common to the two embodiment being omitted from FIG. 3.

Figure 1:
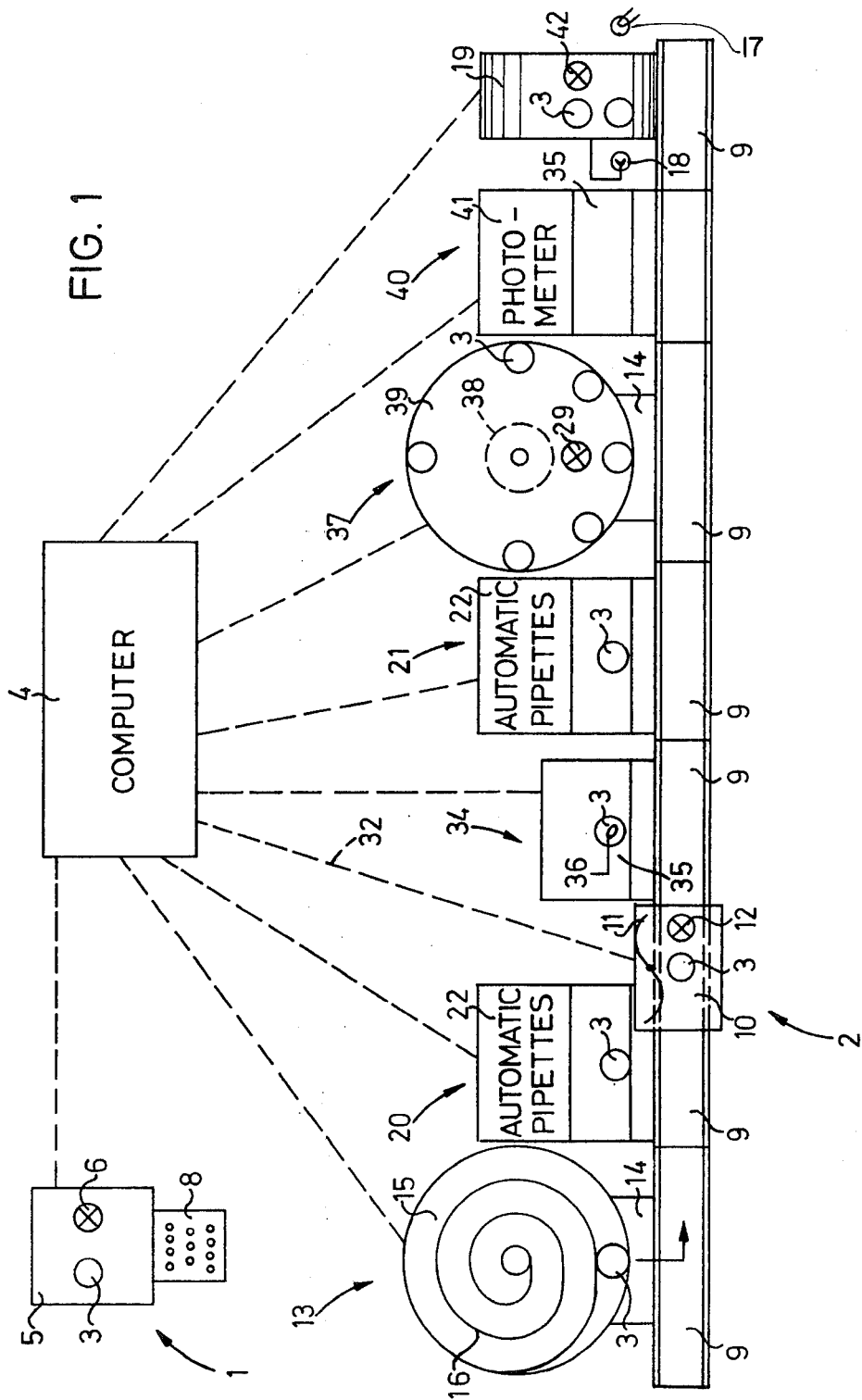
FIG. 1 shows a first embodiment of the invention in a simplified top plan view.

The analysis arrangement shown in FIG. 1 essentially consists of a programming station 1, the analysis machine 2 proper, a battery of plastic beakers 3 as specimen containers, and a computer 4.

The programming station 1 has a flat horizontal platform 5 carrying a reading head 6 which is essentially a vertical array of four photoelectric cells. As is better seen in FIG. 2, each beaker 3 carries four axially spaced circumferential identification bands 7 which may be either white or black and are horizontally aligned with respective cells of the reading head 6 when the beaker stands on the platform 5. The pattern of black and white bands on each beaker 3 is different and provides a binary identification code for 15 beakers which may be read by the head 6 and transmitted to the computer 4 in a manner conventional in itself and not specifically illustrated. A keyboard 8 permits an operator to trigger the head 6 for transmission of the beaker code and further to provide the computer 4 with information on the specimen in the beaker.

The analysis machine 2 is assembled from modular units which each include a straight section of a track 9. A self-propelled carriage 10 can move back and forth on the assembled track. An S-shaped bar 11 is mounted on the flat top of the carriage 10 and may rotate in a horizontal plane about its center, as will be described in more detail hereinbelow. A reading head 12 is mounted on the carriage 10 sufficiently above the carriage top not to interfere with movement of the bar 11.

The first of the several operating stations arranged in a row along the track 9 is a feeding station 13 which essentially consists of a base 14 carrying a horizontal turntable 15 and a spiral-shaped guide baffle 16 fixedly mounted on the base 14, the turns of the spiral being spaced for guiding beakers 3 on the rotating turntable 15 radially outward from the center of the latter. A light source 17 and a photoelectric cell 18, arranged substantially as shown with reference to a discharge conveyor 19, but omitted from other operating stations in order not to crowd the drawing, interrupt the electric current supply to a motor (not shown) in the base 14 when the presence of a beaker 3 on the container supporting turntable 15 adjacent the associated track section is sensed, thereby interrupting the normal, continuous, clockwise rotation of the turntable 15.

A first pipetting station 20 follows the feeding station 13, and a second pipetting station 21, not significantly different from the station 20, is the fourth element in the row of operating stations, both stations including bases and multiple automatic pipettes 22 controlled by the computer 4.

The carriage 10, as shown in FIG. 2, has four wheels 23 which roll on the track 9, and two of the wheels are driven by a reversible electric motor 24 through a speed reducing transmission 25 which includes a magnetic clutch and an electrically operated brake for its output shaft, as is conventional in itself and not shown in detail. The motor 24 and transmission 25 are mounted on the underside of the carriage body 26 which is a flat plate having lateral, depending skirts 27, the shafts of the wheels 23 being journaled in the skirts. The vertical shaft 28 of the bar 11 is driven by the motor 24 through another transmission, closely similar to the transmission 25 and obscured by the motor 24 in FIG. 2. A bracket 30 on the top surface of the carriage body 26 supports the reading head 12. The head 12, the motor 24, and the transmissions are controlled by a control circuit including necessary relays and a timing switch in a housing 31 which is mounted on the underside of the body 26. The elements in the control housing are connected to the computer 4 by a flexible cable 32 (FIG. 1) for receiving electric power and control signals. A limit switch 33 on a skirt 27 is actuated by a cam (not shown) on each of the operating station bases to transmit an initiating signal to the control circuit in the housing 31.

As shown in FIG. 1, the carriage 10 is about to enter a position of alignment with a mixing station 34 whose base carries a supporting platform 35 identical with corresponding platforms of the pipetting stations 20, 21. A rotating electromagnet obscured below the non-magnetic platform 35 stirs the contents of a beaker 3 placed on the platform and containing a plastic-coated stirring rod 36. Corresponding rods are normally also present in all other beakers 3, but have not been shown.

The second pipetting station 21 is followed by a holding station 37 which essentially consists of a base 14 enclosing an indexing electric motor 38 and a circular platform 39 mounted on the vertical output shaft of the motor 38. A reading head 29 fixedly mounted on the base 14 in a manner not specifically shown can read the code on a beaker 3 located adjacent the track 9 on the platform 39.

A photometer station 40 is arranged between the holding station 37 and the discharge conveyor 19. It includes an automatic photometer 41 which is a staple article of commerce not capable of detailed illustration on the scale of FIG. 1. An intake tube of the photometer is lowered into a beaker 3 placed on the supporting platform 35 of the photometer, and a pump in the photometer draws liquid from the beaker through a cuvette arranged between a filtered light source and a photoelectric cell, the cell transmitting its reading to the computer 4.

The base of the discharge conveyor 19, obscured in FIG. 1, carries a stationary reading head 42 for identifying beakers 3 being moved away from the track 9 as soon as their presence is detected by the photoelectric cell 18. The operating elements associated with the conveyor 19 are connected to the computer 4 as are those of all other stations.

The apparatus shown in FIGS. 1 and 2 is operated as follows:

An operator introduces a weighed specimen and a stirring rod 36 into an empty beaker, places the beaker on the platform 5 of the programming station 1, and presses keys of the keyboard 8 to actuate the reading head 6 and to transmit to the computer 4 the serial number and the weight of the specimen and the sequence of operations to be performed. He then places the beaker near the center of the baffle 16. After completion of the analysis, he receives from the computer a printout carrying the serial number of the specimen and the analysis result.

The rotating turntable 15 shifts the beaker 3 to the illustrated position adjacent the track 9 and then stops. The computer 4 signals the carriage 10, when empty, to move into alignment with the feeding station 13. When such alignment is signaled to the computer by the switch 33, the bar 11 is swung from the illustrated traveling position clockwise through an angle of 270° and then counterclockwise through an angle of 90° so that the beaker is transferred from the turntable 15 to the carriage, and the rod 11 is returned to its illustrated normal position, the motor 24 being reversed from time to time, and the magnetic clutches and brakes of the transmissions 25 being energized by the controls in the housing 31 as needed to perform the desired operations, as is conventional in itself.

Upon completion of the transfer and disengagement of the transmission for the rod 11, the carriage is moved to a pipetting station 20, 21 where the beaker 3 is transferred to the supporting platform while the empty carriage 10 is available to receive and transfer another beaker. The computer 4 responds to alignment signals from the switch 33 to stop the carriage at a station corresponding to the program for the beaker carried thereon as identified by the reading head 12 while passing operating stations not needed by the beaker at the specific time of alignment.

The beaker transferred from the carriage 10 to the pipetting station having been identified to the computer 4 by the reading head 12, the pipetting station is caused to introduce a programmed amount of a programmed liquid into the beaker, whereupon the beaker is ready to be moved further by the carriage 10. Additional liquid may be supplied from the same or the other pipetting station, and each added liquid is mixed with the previous contents of the beaker at the mixing station 34 in a manner obvious from the preceding description. The contents of the beaker are partly withdrawn at the photometer station 40, and the beaker thereafter is discharged into a collecting receptacle, not shown, by the discharge conveyor 19.

If a waiting time is needed after addition of a reagent to the contents of a beaker 3, and before the specimen mixture is ready for the next operation, the beaker is placed on the platform 39 of the holding station 37 and transferred to the carriage 10 when it is identified by the reading head 29 after a suitable number of revolutions of the platform 39, the motor 38 being stopped by the computer 4 for the brief period necessary for arrival of the carriage 10. If, at this time, the carriage holds another beaker requiring transfer to the holding station 37, the afore-described movement of the rod 11 causes simultaneous transfer of one beaker from the holding station to the carriage and of another beaker from the carriage to the holding station.

The operation of the analysis machine 2 will be further illustrated by the following Example.

EXAMPLE 1

A process liquid containing a primary amine contaminated by the corresponding secondary amine was to be analyzed every 10 minutes for the concentration of the latter. The operator weighed out specimens of approximately 24 mg from time to time and placed beakers 3 containing the specimens on the turntable 15 after suitably programming the computer 4 as described above.

The beaker was transferred to the first pipetting station 20 where 2 ml isopropanol and 2 ml of a 10% salicylaldehyde solution in propanol were added, the mixture being homogenized at the mixing station 34. It was then stored 20 minutes at the holding station 37 and thereafter transferred to the pipetting station 21 for addition of 2 ml indicator solution (30 mg bromocresol green and 0.4 ml 0.1 N NaOH in enough isopropanol to make 200 ml). After being homogenized at the mixing station 34, an aliquot of the reaction mixture was evaluated by the photometer 41, and the remainder discarded after discharge of the beaker by the conveyor 19.

While the Example illustrates the sequential analysis of specimens of the same type for a single component, the track 9 may be lengthened to include additional operating stations for performing multiple analyses of the same specimen or analyses of different specimens for different components utilizing only those operating stations illustrated in FIG. 1 which are common to both analysis programs. A beaker 3 was moved back and forth on the track 9 in Example 1 to reach the mixing station 34 three times while at least two other beakers were in the machine 2. Obviously, many more beakers can be accommodated simultaneously and transferred by the single carriage 10 expeditiously. However, the use of more than one carriage has been found convenient in machines of the illustrated type which have more stations than are shown in FIG. 1, particularly when several very different sequences of operations are to be performed on the contents of different beakers, and few sequences include an extended holding period.

In a machine of the invention capable of performing different types of analyses, operating stations including automatic titrators, automatic chromatographs, and other automatic analysis devices, conventional in themselves, may be employed in a manner obvious from the description of FIG. 1. If the automatic equipment of the machine does not permit a step of the desired analytical method to be performed, the beaker carrying the specimen may be discharged partly by the conveyor 19, but the conveyor stopped and an audible or visual signal generated when the beaker reached the reading head 42 of the discharge conveyor so that the operator may withdraw the beaker and manually perform the operation which is too infrequent to warrant the installation of a suitable automatic operating station.

When the nature of the analyses to be performed permits, the track 9 and carriage 10 shown in FIG. 1 may be replaced by a continuous conveyor moving in a closed loop in one direction only as is shown in FIG. 3.

The modified apparatus of FIG. 3 includes a programming and feeding station 42 whose platform 43 is equipped with a reading head 6 of the afore-described type for reading identification bands on a plastic beaker 3 manually placed on the platform 43. The station 42 also includes a keyboard, substantially identical with the keyboard 8 described with reference to FIG. 1, and omitted from FIG. 3. A bar 11' which is approximately J-shaped or one half of the afore-described S-shaped bar 11 is mounted on the platform 43 for sweeping a beaker 3 positioned for reading by the head 6 to a conveyor 44.

As is conventional in itself, the conveyor includes a chain 44' trained over non-illustrated guide and drive pulleys in a closed loop, and evenly spaced links of the chain 44' carry trays 45 for movement in a horizontal path, each tray being flush with the platform 43 and corresponding platforms of other operating stations of the apparatus. The trays are closely juxtaposed to the platforms during their travel. The bar 11' is swung on its vertical shaft by a motor under the platform 43.

Adjacent the programming and feeding station 42 in the clockwise direction of conveyor movement, as viewed in FIG. 3, a first pipetting station 46 has a platform similar to the platform 43 and a set of automatic pipettes 47. Additionally, the platform carries an S-shaped bar 11 and a reading head 12' located for identifying a beaker 3 which approaches the station 46. The magnetic stirrer 48 is built into the platform of the station 46. A second pipetting station 49 is the fourth operating station of the analysis arrangement and is identical with the station 46.

The third station is a pumping station 50 whose container supporting platform may be identical with those of the pipetting stations 46, 49, but does not need a magnetic stirrer. It includes a small metering pump 51 whose intake pipe may be moved into a beaker 3 on the platform for removing and discarding a portion of the beaker contents. The pumping station 50 is followed by the aforementioned second pipetting station 49, and thereafter by a photometer station 52, analogous to the afore-described station 40, but having a container supporting platform 53 flush with and contiguously adjacent the passing trays 45. The platform 53 is equipped with an S-shaped, rotary bar 11 and a reading head 12'. The normal run of a beaker 3 terminates at a discharging station 54, essentially consisting of a table or platform carrying a J-shaped bar 11' and a reading head 12'.

The non-illustrated drive of the conveyor 44 and the several stations 42, 46, 50, 49, 52, 54 are connected by a computer for operation in timed sequence, as more specifically described with reference to FIGS. 1 and 2. The trays 45 travel continuously unless a beaker 3 identified by a head 12' at one of the stations needs to be transferred to that station. The conveyor then is stopped so that the identified beaker may be transferred to the container supporting platform of the station by a bar 11, 11'. The conveyor 44 is similarly stopped when a beaker 3 is ready to leave a station whose reading head senses the approach of an empty tray 45.

The analysis arrangement shown in FIG. 3 may be operated in the manner described in the following Example.

EXAMPLE 2

Tablets were to be analyzed for their content of dimenhydrinate by a method derived from Method No. 32, April 1972, of the Drug Autoanalysis Manual of the Public Health Service, Food and Drug Administration. Individual tablets were taken at random at intervals of a few minutes by an inspector from a production run and inserted in beakers 3 together with magnetic stirring rods, not shown. The beakers were then placed sequentially on the platform 43 of the programming and feeding unit on a marked spot in front of the reading head 6. Operation of the non-illustrated keyboard by the inspector caused the identifying indicia of the beaker to be read into the computer memory together with the processing program for the beaker which began with transfer of the beaker to the first available tray 45 by the bar 11'.

Upon arrival of the beaker alongside the first pipetting station 46, the conveyor 44 was stopped long enough to permit the beaker to be swept from its conveyor tray to a spot above the stirrer 48 and within range of one of the automatic pipettes 47 which charged the beaker with 100 ml of a mixture of 1 volume concentrated hydrochloric acid and 100 parts water. The stirrer 48 thereafter was energized to disintegrate the tablet and to dissolve the dimenhydrinate uniformly in the liquid.

The beaker was returned to the conveyor 44 and traveled in the closed conveyor loop on its tray 45 for 30 minutes. The metering pump 51 at the pumping station 50 thereafter removed 95 ml of the liquid from the beaker, and the second pipetting station diluted the residue with 200 ml hydrochloric acid 1:100 and thoroughly mixed the diluted solution which was ultimately transferred to the photometer 52 for analysis at 276 nm. By comparing the output signal of the photometer 52 with an output signal produced by a reference tablet of known composition, the non-illustrated computer produced a read-out identifying the analyzed sample and indicating its dimenhydrinate content.

When equipped with suitable pipettes and liquids at the pipetting stations 46, 49, the apparatus of FIG. 3 can perform the method of EXAMPLE 1 with minor modifications, and may perform the methods of Examples 1 and 2 simultaneously. A beaker 3 carrying a sample to be analyzed by the method of Example 1 is fed to the conveyor 44 as described in Example 2, mixed with isopropanol and salicyclaldehyde at the first pipetting station 46, stored 20 minutes on a circling tray 45, mixed with indicator at the second pipetting station 49, and analyzed by the photometer 52, the unused remainder of the reaction mixture being discarded at the discharging station 54. The portion of the conveyor 44 between the station 54 and the programming station 42 is accessible, the beakers may be permitted to pass the discharging station for later manual removal to a manually performed analysis step, if so desired.

The method of Example 1 does not require the pumping station 51, and a tray carrying a sample to be analyzed by the method of Example 1 does not stop at the pumping station which may simultaneously operate on a liquid undergoing the procedure of Example 2. Beakers carrying samples for both methods may be stored simultaneously on respective trays 45 of the conveyor 44 for the necessary periods.

When employed for repeatedly performing the same sequence of operations in quick succession, the analysis arrangements of the invention may perform rapidly and without limitation to the slowest individual step by the use of several operating stations for performing the slowest step which are arranged sequentially along the specimen path, a station occupied by a preceding specimen being by-passed by the following specimen to reach another operating station of the same kind. When apparatus according to this invention is employed for performing procedures requiring the same step to be carried out repeatedly, and the step is short enough relative to the rate of specimens entering the apparatus, the same specimen may be returned repeatedly to the same station without being hampered by other specimens in the apparatus at the same time. In either case, the operating stations may be utilized more efficiently than in an in-line analysis apparatus having operating stations of comparable capacity. A large number of different procedures can be performed on a single apparatus of the invention without mutual interference of specimens undergoing different sequences of operations. As a rule, the dwell time of a specimen in an apparatus of the invention is shorter than in conventional in-line apparatus because of the omission of waiting periods not required by the nature of the analysis to be performed.

The apparatus shown in FIGS. 1 and 2 has the added advantage that it can be modified quickly to perform radically different sequences of operations because of its modular construction. The individual stations may be arranged along the track in a sequence not necessarily following the sequence in which they are visited by a specimen, and little time is lost in a procedure in which a specimen is repeatedly carried back and forth along the row of operating stations. The apparatus of FIG. 3 is capable of transferring specimens between stations not adjacent each other in the direction in which the specimen carrying trays travel on the track provided by the chain 44', but time is spent while the specimen travels over a major portion of the conveyor loop to reach the next station when that station precedes the station last visited in the direction of conveyor travel.

The operating stations employed in the apparatus of the invention are not limited to those specifically described with reference to the drawing, and any conventional or novel operating station capable of remote control may be substituted for the devices specifically mentioned to suit the intended purpose. While a magnetic stirrer has been referred to in the description for the sake of simplicity, more complex mechanical agitators are commonly employed in this art and may be substituted for the magnetic stirrers without departing from the spirit and scope of the invention. Operation at room temperature has been chosen in the Examples in order to avoid description and pictorial representation of heating, cooling, and temperature control devices, conventional in themselves and not directly relevant to this invention, but such accessories will be built into apparatus of the invention by those skilled in the art without requiring specific guidance.

The bars 11, 11' which sweep containers from carriers on the conveyor track, such as the carriage 10 and the trays 45, to container supporting platforms of the individual operating stations, are merely illustrative of the transfer devices which are essential to this invention, but may be very different in structure and function from the simple bars 11, 11' to accommodate specimen containers other than flat-bottomed beakers and to suit container supports which are not on the same level nor directly contiguous a carrier on the conveyor track.

It should be understood, therefore, that the foregoing disclosure relates only to presently preferred embodiments of the invention, and that it is intended to cover all changes and modifications of the examples of the invention chosen herein for the purpose of the disclosure which do not constitute departures from the spirit and scope of the invention set forth in the appended claims.

What is claimed is:

1. Analysis apparatus comprising, in combination:
   (a) track means defining an elongated path;
   (b) carrier means adapted to move on said track means in said path while carrying a container;
   (c) a plurality of station means spaced along said path, each station means including a container support adjacent said path;
   (d) drive means for moving said carrier means on said track means; p1 (e) transfer means adjacent said path for transferring a container between said carrier means and the container support of each of said station means when the carrier means is aligned with the station means transversely of said path, (1) said transfer means including means for moving a container from said carrier means to the container support of a predetermined station means, and for simultaneously moving another container from the container support of said predetermined station means to said carrier means, (2) one of said station means including dosing means for introducing a predetermined amount of liquid into a container supported on the container support of said one station means, (3) another station means including analyzing means for analyzing the contents of a container transferred to the container support of said other station means; and (f) control means for operating said drive means, said transfer means, said dosing means, and said analyzing means in timed sequence.

2. Apparatus as set forth in claim 1, wherein the container support of a further one of said station means includes a plate member mounted for rotation about an upright axis, and said transfer means include a stationary guie member having the approximate shape of a spiral centered in said axes, said guide member being upwardly offset from said plate member.

3. Apparatus as set forth in claim 1, wherein said path extends in a closed loop.

4. Apparatus as set forth in claim 1, wherein said analyzing means includes signal generating means for generating an electrical signal indicative of a property of contents of a container supported on the container support of said other means station.

5. Apparatus as set forth in claim 1, wherein said predetermined station means includes storage means spaced from said container support for storing at least one of said containers remote from said container support.

6. Apparatus as set forth in claim 5, wherein said predetermined station means further includes conveying means for conveying said at least one container between said container support and said storage means.

7. Apparatus as set forth in claim 1, wherein said transfer means include actuating means movably mounted on said carrier means for engagement with a container on said carrier means and for moving the engaged container from said carrier means to the container support of an aligned station means.

8. Apparatus as set forth in claim 7, wherein said actuating means include an actuating member mounted on said carrier for rotary movement about an axis transverse to said path, a portion of said member spaced from said axis engaging said container during said moving of the engaged container.

9. Apparatus as set forth in claim 1, wherein said control means include reading means for reading indicia on a container carried by said carrier means when said carrier means is aligned with one of said station means.

10. Apparatus as set forth in claim 9, wherein said reading means is mounted on said carrier means.

11. Apparatus as set forth in claim 9, wherein said reading means is mounted on said container support.

12. Analysis apparatus comprising, in combination:

(a) track means defining an elongated path extending in a closed loop;

(b) a plurality of carriers evenly spaced on said track means along said loop;

(c) a plurality of station means spaced along said path, each station means including a container support adjacent said path;

(d) drive means for simultaneously moving said carriers in said path, each carrier including carrying means for carrying a container through each portion of said path;

(e) transfer means adjacent said path for transferring a container between each carrier and the container support of each of said station means when the carrier is aligned with the station means transversely of said path, (1) one of said station means including dosing means for introducing a predetermined amount of liquid into a container supported on the container support of said one station means, (2) another station means including analyzing means for analyzing the contents of a container transferred from one of said carriers to the container support of said other station means; and (f) control means for operating said drive means, said transfer means, said dosing means, and said analyzing means in timed sequence.

13. Apparatus as set forth in claim 12, wherein the number of said carriers is greater than the number of said stations.

14. Apparatus as set forth in claim 13, wherein said drive means include a conveying member extending in said loop, said carriers being fastened permanently to respective, evenly spaced portions of said conveying member.

* * * * *

UNITED STATES PATENT AND TRADEMARK OFFICE
CERTIFICATE OF CORRECTION

PATENT NO. : 4,113,436

DATED : September 12, 1978

INVENTOR(S) : Roger Daniel Werder et al.

It is certified that error appears in the above-identified patent and that said Letters Patent are hereby corrected as shown below:

Claim 1, line 9, cancel " pl "

Signed and Sealed this

Seventh Day of November 1978

[SEAL]

Attest:

RUTH C. MASON
Attesting Officer

DONALD W. BANNER
Commissioner of Patents and Trademarks